United States Patent [19]

Boulay et al.

[11] Patent Number: 4,654,529
[45] Date of Patent: Mar. 31, 1987

[54] METHOD FOR MEASURING THE FIBRE ORIENTATION ANISOTROPY IN A FIBROUS STRUCTURE

[75] Inventors: Russell Boulay, Cap Rouge; Bernard Drouin, Ste Foy; Richard Gagnon, Cap Rouge, all of Canada

[73] Assignee: Universite Laval, Cité Universitaire, Canada

[21] Appl. No.: 823,459

[22] Filed: Jan. 28, 1986

[51] Int. Cl.[4] ............................................. G01N 21/21
[52] U.S. Cl. ................................ 250/341; 250/358.1; 250/225; 250/359.1; 356/364
[58] Field of Search ................ 162/263; 356/369, 364; 250/225, 341, 358.1, 359.1

[56] References Cited

U.S. PATENT DOCUMENTS

| | | | |
|---|---|---|---|
| 2,509,068 | 5/1950 | McMahon | 250/225 |
| 2,824,488 | 2/1958 | Bridges et al. | 250/225 |
| 3,807,868 | 4/1974 | Simila | 356/118 |
| 4,171,916 | 10/1979 | Simms et al. | 356/366 |

FOREIGN PATENT DOCUMENTS

| | | | |
|---|---|---|---|
| 160304 | 11/1985 | European Pat. Off. | 356/364 |
| 2514494 | 4/1983 | France . | |

*Primary Examiner*—Carolyn E. Fields
*Attorney, Agent, or Firm*—Robic, Robic & Associates

[57] ABSTRACT

A method and a device for measuring the fibre orientation anisotropy in a fibrous structure such as a sheet of paper or a textile. According to this method, a linearly polarized, far infrared laser beam is directed towards one side of the fibrous structure whose fibre orientation anisotropy is to be measured. The incident energy of the laser beam is measured before this beam traverses the fibrous structure, and its transmitted energy is measured on the other side of the fibrous structure. The transmission coefficient T of the laser beam is determined in at least two different orientations of the polarization plane of the beam with respect to the fibrous structure, this coefficient T being the ratio of the transmitted-to-incident energies. This coefficient T varies exponentially with the basis weight of the fibrous structure and the ratio $\alpha$ of the absorption coefficients that can be derived from two measurements of coefficient T in two different orientations of the polarized beam, gives a quantitative evaluation of the amount of fibre orientation anisotropy, the value of this ratio $\alpha$ be equal to 1 when no anisotropy is present in the fibrous structure.

22 Claims, 14 Drawing Figures

METHOD FOR MEASURING THE FIBRE ORIENTATION ANISOTROPY IN A FIBROUS STRUCTURE

BACKGROUND OF THE INVENTION (a) Field of the invention

The present invention is concerned with a method for determining the fiber orientation in a sheet structure made of fibers or containing such fibers, such as a sheet of paper, a cardboard, a sheet of textile or fiberglass, etc...

More particularly, the invention is concerned with a method for quantitatively and locally measuring the fiber orientation anisotropy in a fibrous structure, and with a device for carrying out such a method.

(b) Brief description of the prior art

Quantitative measurement of the fiber orientation anisotropy in a fibrous structure is very important in some industries, such as, in particular, the paper making industry, in order to control and possibly adjust the quality of the paper being made, especially its strength, its behaviour to moisture, its resistance to drying stresses and its dimensional stability.

Indeed, it is well known that numerous factors such as parameters of manufacture or designs of machinery may substantially influence the general orientation of the fibers in a fibrous structure being made. In the paper making industry such factors are, by way of non-restrictive examples:

the shape of the lips at the outlet of the head box from which exits the pulp;

the differential velocity between the pulp and the belt on which it is deposited;

the vibration of the belt; and the subsequent calendering.

Of course, the non-uniform distribution and/or orientation in the machine direction (M.D.) and cross-direction (C.D.) of the fibers in the sheet of paper that is being made because of one or more of the above listed factors, significantly affects the strength and general behaviour of this sheet and makes it of good or poor quality.

Several methods for determining the fibre orientation and, preferably, quantitatively measuring the fibre orientation anisotropy, are known in the art and some of them are commonly used in the industry.

By way of examples, fibre orientation anisotropy in paper can be measured directly by incorporating to the pulp a certain amount of dyed fibres and observing these fibres with a microscope in the finished sheet (see CROSBY, C. M. et al, Tappi, 103-106, March, 1981). However, such a method is combersome and cannot be used easily in a production plant.

Another method of measuring fibre orientation anisotropy is the one known as "zero-span tensile strength test" (see ANCZUROWSKI, E. et al, Pulp and Paper, 112-115, December 1983). This method which basically consists in measuring the force necessary to tear apart a piece of paper hold between two pairs of jaws is known to be very reliable, and is relatively easy to apply in normal paper production by using it on selected samples. On the other hand, this method is destructive and statistical in nature and thus cannot be used to find out how the fibre orientation anisotropy varies from point to point in the sample, and how this variation is related to other physical properties.

Several methods have also been proposed for measuring local variations of fibre orientation anisotropy, based on the analysis of the diffraction and/or scattering patterns of a visible laser light incident on paper (see, RUDSTROW L. et al, Svensk Papperstidnig, 117-121, March 1970). This technique which has been successfully developped to industrial standards, has the advantage of being non-destructive, but its basic principle calls for a very sophisticated data analysis in order to attain the requested level of precision. Moreover the visible light diffraction depends mostly on the surface condition and does not give any indication regarding the average anisotropy through the whole thickness of the sample.

French laid-open patent application No. 2,514,494 MICRAUDEL SARL discloses a method of determining the fibre orientation anisotropy of a fibrous structure, which is also based on the analysis of the diffraction patterns of a polarized laser light traversing the fibrous structure. The optical pattern of the structure, which is so obtained, is recorded and interpreted to determine the actual distribution of the light intensity as a function of the angular position of the plane of polarization of the laser light, or of the structure.

In practice, such an interpretation which is not disclosed is the French laid-open application is very complicated and slow to carry out, thereby making this method not usable on line. Moreover, this method can only be used with thin paper to avoid that too much extinction of the laser light through the paper makes the diffractions pattern difficult or even impossible to record and interpret.

Still another method of measuring paper anisotropy is based on ultrasonic velocity measurements (see FLEISCHMAN, E. H. Ph.D. thesis, The Institute of Paper Chemistry, Lawrence University, 1981, or BAUM A. G. et al, Tappi, vol. 62, No. 5, May, 1979). This technique is interesting in that it can be used in line, but it usually has a spatial resolution around 3 cm and its results are dependent on many mechanical characteristics of the paper sheet (young's modulus, density, etc.)

Last of all, a further method for determining the fibre orientation in paper is disclosed in U.S. Pat. No. 3,807,868 to VALMET OY. According to this method, a polarized laser light beam is directed at right angles to the surface of the paper and the intensity of the reflected light is measured by means of two polarizers. This technique is interesting in that it can be used on line and it gives an index value for the fibre orientation anisotropy. However, it has the drawback of being a surface measurement technique, which gives no indication regarding the average anisotropy through the whole thickness of the sample.

SUMMARY OF THE INVENTION

An object of the present invention is to provide a non-destructive method for quantitatively measuring the fibre orientation anisotropy of a fibrous structure, which method is fast and easy to carry out and can be used on line in any industrial machine for manufacturing sheet of fibrous material, such as a paper making machine.

Another object of the invention is to provide such a non-destructive method which gives very precise results that are independent of the surface condition or mechanical characteristics of the fibrous structure, and are fully correlated with the results obtainable with standard technique such as the well-known zero-span tensile strength test.

A further object of the invention is to provide such a non destructive method which makes use of a far infrared or submillimeter laser beam traversing the fibrous structure whose anisotropy is to be measured, thereby giving an indication of the average fibre orientation anisotropy through the whole thickness of the sample.

Still another object of the invention is to provide a device for carrying out the above non-destructive method, which device can be implemented for use in labs or on line on an industrial machine.

In accordance with the invention, these objects are achieved with a method for measuring the fibre orientation anisotropy in a fibrous structure, comprising the steps of:

- directing a linearly polarized, far-infrared laser beam having a wavelength preferably ranging between 50 and 2000 micrometers towards one side of the fibrous structure whose fibre orientation anisotropy is to be measured;
- measuring the incident energy of said laser beam before it traverses the fibrous structure;
- measuring the transmitted energy of the laser beam on the other side of the fibrous structure with a first laser beam energy detector;
- determining the transmission coefficient T in at least two different orientations of the polarization plane of the beam with respect to the flat fibrous structure, this coefficient T being the ratio of the transmitted-to-incident energies;
- provided that both reflection and scattering of the laser beam by the fibrous structure remain small as compared to absorption and, thereby, that:

$$T = e^{-Ab}$$

where e is 2;71828; A is the absorption coefficient of the structure and b is the basis weight of the structure, calculating the ratio $\alpha$ of the absorption coefficients A measured in the at least two different orientations of the polarization plane of the beam; and using the so calculated absorption coefficient ratio $\alpha$ as a quantitative evaluation of the amount of anisotropy. the value of this absorption coefficient ratio $\alpha$ being equal to 1 when no anisotropy is present in the fibrous structure.

In accordance with a preferred embodiment of the invention, the incident energy of the laser beam is measured with the first laser energy detector before insertion of the fibrous structure, part of the incident energy of the laser beam being diverted towards a second laser beam energy detector. This diverted incident energy measured with said second detector, is permanently used to normalize to the original value of the incident energy measured.

The fibrous structure may be rotated with respect to the polarization plane of the laser beam in order to achieve determination of the transmission coefficient T in at least two different orientations. Alternatively, the polarization plane of the laser beam may be rotated with respect to the flat fibrous structure in order to achieve this determination. In both cases, provided that the method be used on a fibrous structure having a known machine direction and a known cross-direction, the transmission coefficient T is determined in two orientations: one orientation being parallel to the machine direction of the structure, the other orientation being parallel to the cross-direction of this fibrous structure. If the machine direction of the structure is not known, the coefficient T will have to be determined in more than two orientations, such as, for example, in ten different angular orientations ranging from 0° to 90°.

In accordance with another preferred embodiment of the invention, the method may comprise the additional steps of:

- splitting the linearly polarized laser beam before it traverses the fibrous structure;
- modifying the angle of polarization of one of the splitted beams before it traverses the fibrous structure;
- measuring the transmitted energy of both of these splitted beams on the other side of the fibrous structure; and
- using these two measurements to determine two transmission coefficients T, each of said coefficient T corresponding to an orientation of the polarization plane of the laser beam.

This other embodiment is particularly useful in the industry, as it can be carried out on-line during the process of manufacturing the fibrous structure, and thus used as a quality control tool with a possible feedback on the fabrication parameters to correct any discrepancy noted on the course of operation.

As can now be better understood, the method according to the invention is based on the observation made by the inventors that the transmitted-to-incident energy ratio of a penetrating laser beam is dependent on the relative orientation of the fibres of a fibrous structure and of the plane of polarization of the laser beam.

As can also be understood, this method is fast, easy to carry out an non-destructive, thereby making it usable as control means in an industrial machine, such as a paper making machine.

The invention also proposes a device for measuring the fibre orientation anisotropy in a fibrous structure, which device comprises:

- a far-infrared laser for directing a laser beam towards one side of the fibrous structure whose fibre orientation anisotropy is to be measured;
- a linear polarizer for linearly polarizing the laser beam before it reaches the fibrous structure;
- means for measuring the incident energy of the laser beam before it traverses the fibrous structure;
- a first laser beam energy detector for measuring the transmitted energy of said laser beam on the other side of the fibrous structure;
- means for differently orientating the polarization plane of the beam and fibrous structure with respect to each other; and
- processing means for determining the transmission coefficient T in at least two different orientations of the polarization plane of the beam with respect to the fibrous structure, this coefficient T being the ratio of the transmitted-to-incident energies and then, provided that both reflection and scattering of the laser beam by the fibrous structure remain small as compared to absorption and, thereby, that:

$$T = e^{-Ab}$$

where e is 2,71828; A is the absorption coefficient of the fibrous structure and b is the basis weight of the structure, calculating the ratio $\alpha$ of the absorption coefficients A in said at least two different orientations of the polarization plane of the beam, this ratio $\alpha$ giving a quantitative evaluation of the amount of anisotropy present in the fibrous structure.

BRIEF DESCRIPTION OF THE DRAWINGS

The invention will be better understood upon reading the following non-restrictive description given with reference to the accompanying drawings, wherein.

DESCRIPTION OF DIFFERENT PREFERRED EMBODIMENTS

Figure 1:
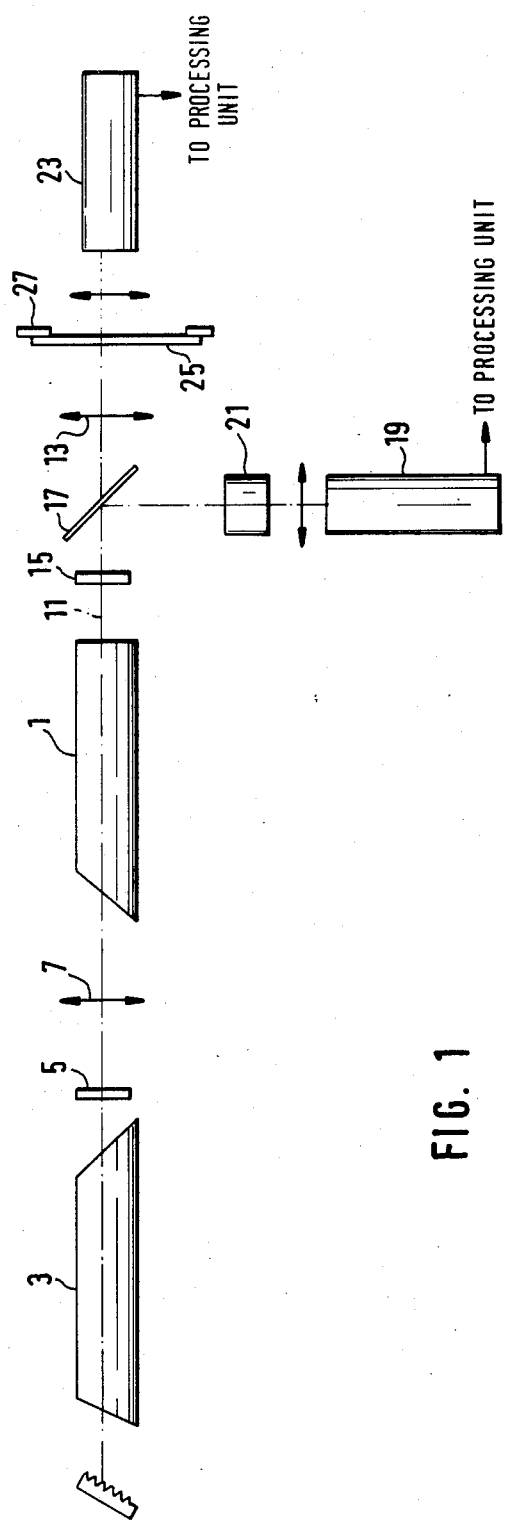
FIG. 1 is a diagrammatic representation of a device according to the invention for use in a laboratory.
Figure 2:
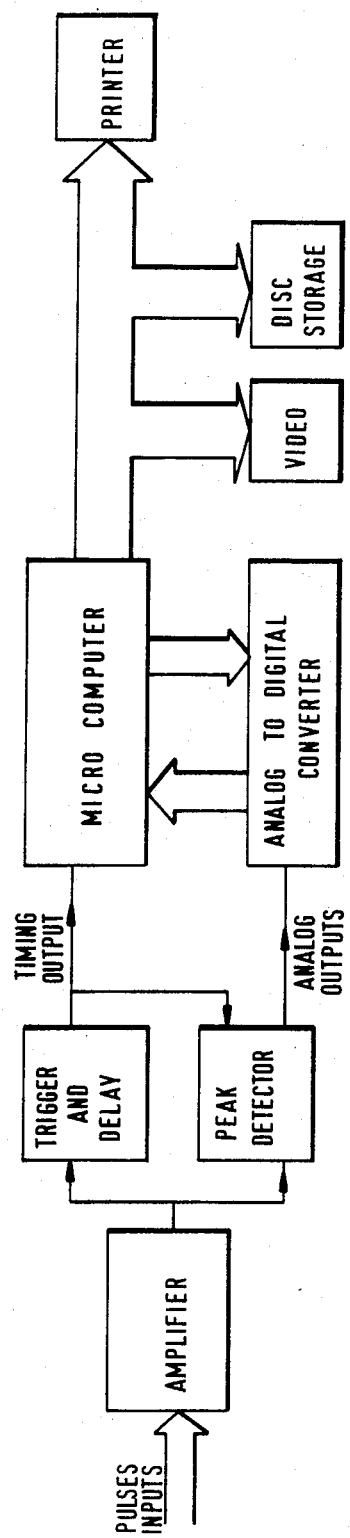
FIG. 2 is a diagrammatic representation of the electronic processing unit of the device of FIG. 1.
Figure 3:
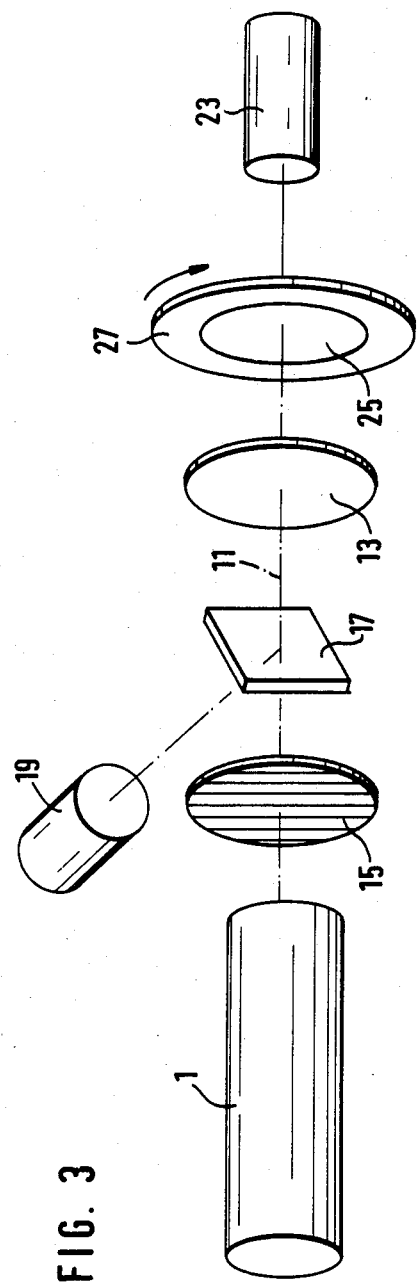
FIG. 3 is a perspective representation of the main elements of the device shown in FIG. 1.

The device according to the invention as shown in FIGS. 1 to 3 comprises a far infrared laser 1 producing a beam of coherent electromagnetic radiations or waves having a wavelength depending on the substance in the laser cavity, the dimensions of the cavity and the way it received its energy. By way of example, use can be made of a submillimetric laser 1 using methanol as active substance, which laser is pumped by a grating tunable pulsed $CO_2$ infrared laser 3 via a piezo-controlled coupler 5 and Ge-lens 7. This laser produces electromagnetic waves in the 70 to 1200 micrometres wavelength range. However, it should be noted that other wavelength range may be obtained, which vary from 50 to 2000 micrometers depending on the kind of far-infrared laser used for producing the electromagnetic waves.

In the tests reported hereinafter, the laser 1 was a methanol submillimeter laser and was operated in a pulse made at a frequency of 10 Hz with a pulse duration of about 500 microseconds. The peak power output was approximatively 20 milliwatts while the average power level stood around 20 microwatts.

The laser beam 11 can be concentrated on an area of a few square millimeters at shorter wave length, by means of a lens 13.

It is worth noting that the large variation of wavelength possible with such a laser makes it very appropriate for paper transmission measurements. Tests carried out by the inventors have shown in the method according to the invention can be used with paper or other similar material having a basis weight varying from 20 $g/m^2$ to more than 2000 $g/m^2$.

The laser beam 11 emitted by the laser 1 is then linearly polarized by a linear transmission polarizer 15 installed at the laser output. A beam splitter 17 is provided between the polarizer 15 and the lens 13 to divert part of the incident energy of the laser beam toward a high sensitivity, laser beam energy detector 19 that can be a Golay cell. If desired, a Fabry-Perot interferometer 21 can be provided between the beam splitter 17 and the energy detector 19 to monitor the wavelength of the laser beam.

Another high sensitivity, laser beam energy detector 23 is provided to collect the transmitted energy behind the fibrous structure which can be, for example, a piece of paper whose fiber orientation anisotropy is to be measured.

In one embodiment of the invention shown in FIG. 3, the fibrous structure to be inspected is mounted on a goniometer 27 (mobile protractor) so that it may be rotated with respect to the plane of polarization of the laser beam. Alternatively, the whole measuring device can be mounted onto a rotable frame and then rotated with respect to the fibrous structure so as to make different measurement at different angles between the plane of polarization of the laser beam and the general axis of the fibrous structure. The latter embodiment can be used, for example, to measure the fibre orientation anisotropy of sheet of paper while the same is manufactured by a paper-making machine.

The outputs of the detectors 19 and 23 are fed to a microcomputer based data acquisition and analysis system. This system which permits real time analysis, is schematically illustrated in FIG. 2 and will not be further detailed, as its basic structure is not an essential point of invention.

As aforesaid in the "Summary in the Invention" hereinabove, the method according to the invention is based on the observation made by the inventors that the transmission coefficient T of a penetrating linearly polarized laser beam is dependent on the relative orientation of the fibres of the fibrous structure to be inspected with respect to the plane of polarization of the laser beam. This transmission coefficient T can be defined as being the ratio of the transmitted-to-incident energies measured, by way of example, by the detector 23 before and after the fibrous structure 25 is positioned to intersect the laser beam 11. This coefficient of transmission T is, in practice, directly related to the basis weight "b" of the fibrous structure by the equation:

$$T = e^{-Ab} \qquad (I)$$

where e is 2.71828; b is the basis weight of the fibrous structure and A is the absorption coefficient of this structure.

It is noteworthy that equation (I) is valid only if both reflection and scattering of the submillimetre waves by the tested structure are small enough as compared to the absorption. However, it appears that this particular condition is satisfied provided that use is made of a far infrared and preferably submillimetre laser.

It is also noteworthy that equation (I) assumes that the energy which is not transmitted is in fact absorbed by the tested structure, and that, consequently, the transmitted energy decreases exponentially with the basis weight of this structure.

Based on the above observation, the inventors have also found that the ratio of two different transmission coefficients T measured with different orientations of the wave plane of polarization, gives a quantitative evaluation of the fibre orientation anisotropy of the fibrous structure. In the case of a sample having a machine direction (M.D.) and a cross-direction (C D), such as a sample of paper industrially manufactured, the ratio of the transmission coefficient Tm measured with the plane of polarization parallel to the MD of the sample, to the transmission coefficient Tc measured with the wave plane of polarization perpendicular to the MD of the sample, that is parallel to the CD of the sample, gives a quantitative evaluation of the amount of anisotropy. This ratio is equal to 1 when no anisotropy is present.

As the ratio Tm/Tc depends on the basis weight, two superimposed samples may yield a larger relative variation of transmission. To avoid this problem, use is made, in accordance with the invention, of another ratio, namely the ratio of the absorption coefficient A measured in one orientation to the absorption coefficient A measured in another orientation.

By way of example, provided that use is made of a sample having a machine direction (MD), use is made, in accordance with the present invention, of the following ratio:

$$\alpha = \frac{\log_e Tm}{\log_e Tc} = \frac{-Amb}{-Acb} = \frac{Am}{Ac}$$

wherein Am is the absorption coefficient in the machine direction and Ac is the absorption coefficient in the cross-direction.

Keeping in mind the above equation, the fibre orientation anisotropy of a fibrous structure can be measured as follows, using the device disclosed hereinabove.

The linearly polarized laser beam 11 produced by the laser 1 is aimed at the fibrous structure 25 which is, for example, a paper sample perpendicular to the beam axis. The ratio of the energy transmitted by the paper to the incident energy is measured while the sample is rotated around the beam axis, using the goniometer 27 to do so. As aforesaid, the transmitted to-incident energy ratio varies as the angle between the plane of polarization of the beam and the paper machine direction of the sample. A minimum usually occurs when this angle is 0 and the maximum is observed at 90°. The relative values of this maximum and minimum, once corrected for basis weight, using the above indicated exponential absorption model, is a valuable and useful indication of the amount of fiber orientation anisotropy in the sample.

Figure 4:
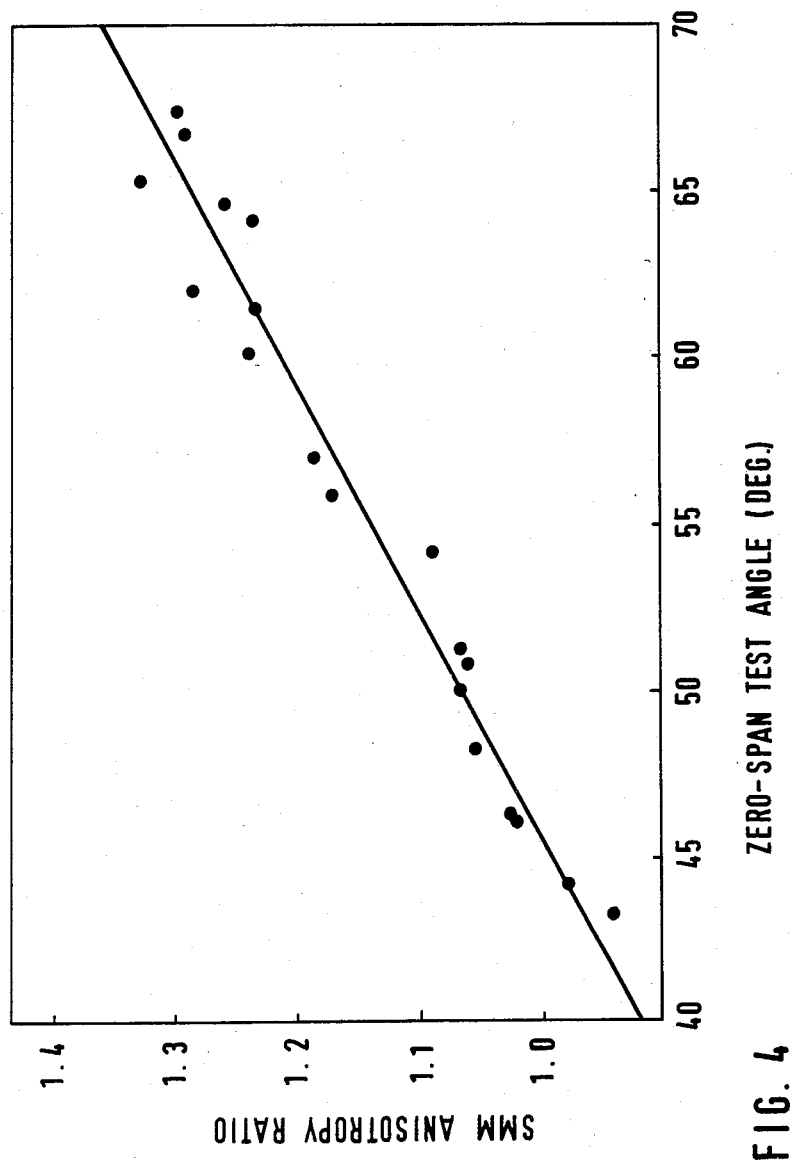
FIG. 4 is a graph obtained with the device of FIG. 1, showing the high correlation between the measurement technique according to the invention and the zero-span tensile strength test for various paper samples.

To validate this method, comparative tests were carried out on paper samples with and without fillers, whose fibre orientation anisotropy had previously been measured with the standard, zero-span tensile strength test. The result of the comparative tests are reported in FIG. 4 and clearly shows that the anisotropy ratio $\alpha$ measured with the device according to the invention is highly correlated to the fiber orientation anisotropy as measured with the zero-span tensile strength test.

A limitation of the experimental procedure described is the incorrect results it would yield if the paper sample has a fibre orientation anisotropy which is not symetrical about its MD. In such a case, two measurements with beam polarisation first parallel, then perpendicular to MD would not indicate the real level of fibre orientation anisotropy. To overcome whis problem one can take many measurements at each point with beam polarization being rorated in small increments; such a procedure requires more time, but it reveals the true fibre orientation distribution.

Thus, an alternative way of measuring the absorption anisotropy ratio $\alpha$ which is more suitable for large paper sample or adaptable onto paper making machine consists in rotating the polarizer 15 or the whole device rather than the paper sample 15. Then, a subsequent transversal displacement of a sample allows a point-to-point anisotropy measurement. Of course, all the energies and position values can be gathered through the microcomputer-based data acquisition system shown in FIG. 2.

When the machine direction and cross-direction of the sample are not known to the operator, it is necessary to measure more than two transmitted-to-incident energy ratio T in order to determine the machine direction of the sample prior to calculating the anisotropy ratio $\alpha$. By way of example, measurement of the transmitted energy can be done onto the sample 25 while the sample angle is varied from 0° to 90° in 10° steps. At each angle, the transmitted-to-incident energy ratio T is determined by averaging over 50 laser pulses (5 seconds) in order to increase the precision. However, with a suitable stabilized laser, a single pulse may be sufficient.

In a typical measurement run, the incident energy of the laser beam can be measured with the detector 23 before insertion of the sample 25, and stored in the memory of the data acquisition system. Thereafter, the diverted part of the incident energy of the laser beam 11 measured by the lateral laser beam energy detector 19 can be used for permanently normalizing the value of the incident energy stored in the data acquisition system.

Figure 11:
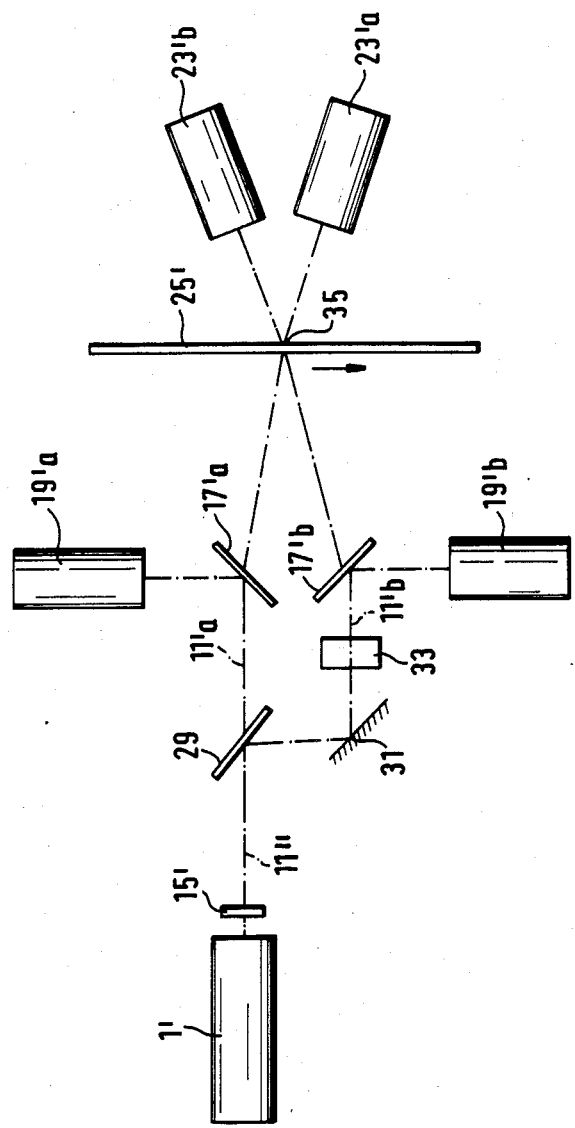
FIG. 11 is a diagrammate representation of a device according to the invention for use on-line in a paper making machine.
Figure 12:
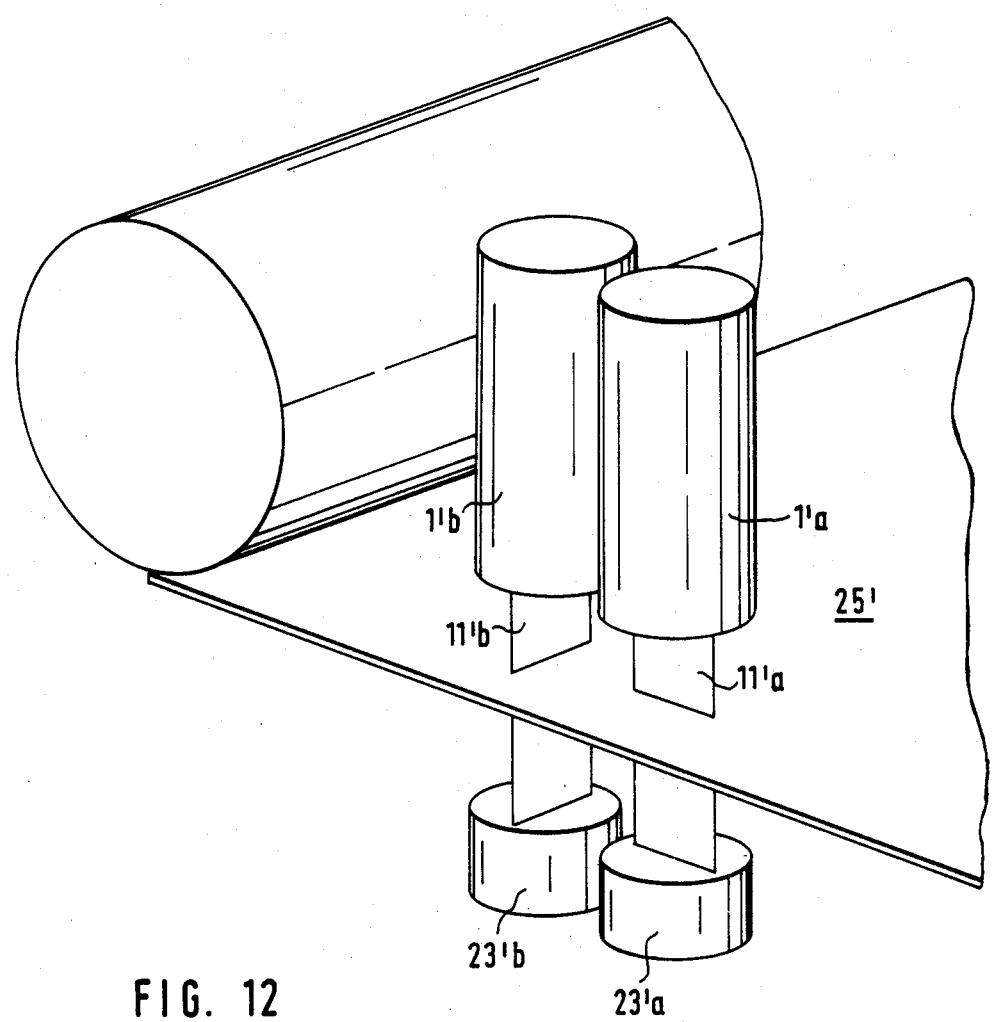
FIG. 12 is a perspective representation of the main elements of the device shown in FIG. 11, according to a variant thereof.

FIGS. 11 and 12 show another embodiment of the invention especially designed for use on an industrial machine, such as, for example, a paper making machine.

Referring to FIG. 11, this device comprises a far infrared laser 1' producing a beam of electromagnetic radiations 11". The beam 11" is linearly polarized by a linear transmission polarizer 15' installed at the laser output. A first beam splitter 29 is provided to split the linearly polarized beam 11" before it reaches the fibrous structure 25' to be inspected. The one splitted beam $11_a'$ is directly aimed at a point 35 of the fibrous structure 25' and its transmitted energy is measured by a laser beam energy detector $23_a'$. The other splitted beam $11_b'$ is reflected on a mirror 31 and passes through a polarizing unit 33 wherein its original axis of polarization is rotated by 90°. The so "rotated" beam $11_b'$ is aimed at the same point 35 of the fibrous structure 25' as the splitted beam $11_a'$ and the transmitted energy is measured by another energy detector $23_b'$ located behind the fibrous structure 25'.

As can be easily understood, the separate detectors $23_a'$ and $23_b'$ both act as the first laser beam energy detector 23 of the embodiment shown in FIG. 1, and simultaneously measure the transmitted energies of both of the splitted beams on the other side of the fibrous structure 25'. The so measured transmitted energy of each of the splitted beam can be supplied to the data acquisition system so that two transmission coefficients T are calculated, one of these coefficients T corresponding to the machine direction of the fibrous structure while the other coefficient T corresponds to a cross direction of this structure.

Of course, means comprising a beam splitter $17_a'$ or $17_b'$ and a second laser beam energy detector $19_a'$ or $19_b'$ may be used for normalizing the value of the incident energy stored in data acquisition system, as was explained hereinabove.

In a variant of this embodiment shown in FIG. 12, use can be made of two parallel lasers $1_a'$ and $1_b'$ to produce two orthogonally oriented laser beam $11_a'$ and $11_b'$, instead of using one single laser 1' as shown in FIG. 11. In this variant, both of the beams $11_a'$ and $11_b'$ may be aimed at a same point of the fibrous structure 25' or may be aimed at two different points spaced apart in the machine direction of the fibrous structure 25'. In this particular case, a timer may be incorporated so that the transmitted energy is measured by the detector $23_a'$ at the same point as it was measured by the detector $23_b'$, due to the linear displacement of the structure 25'.

EXPERIMENTAL RESULTS (1) Confirmation of the validity of the definition of transmission coefficient T Using an experimental device as shown in FIG. 1, different experiments were carried out with two similar paper samples.

Figure 5:
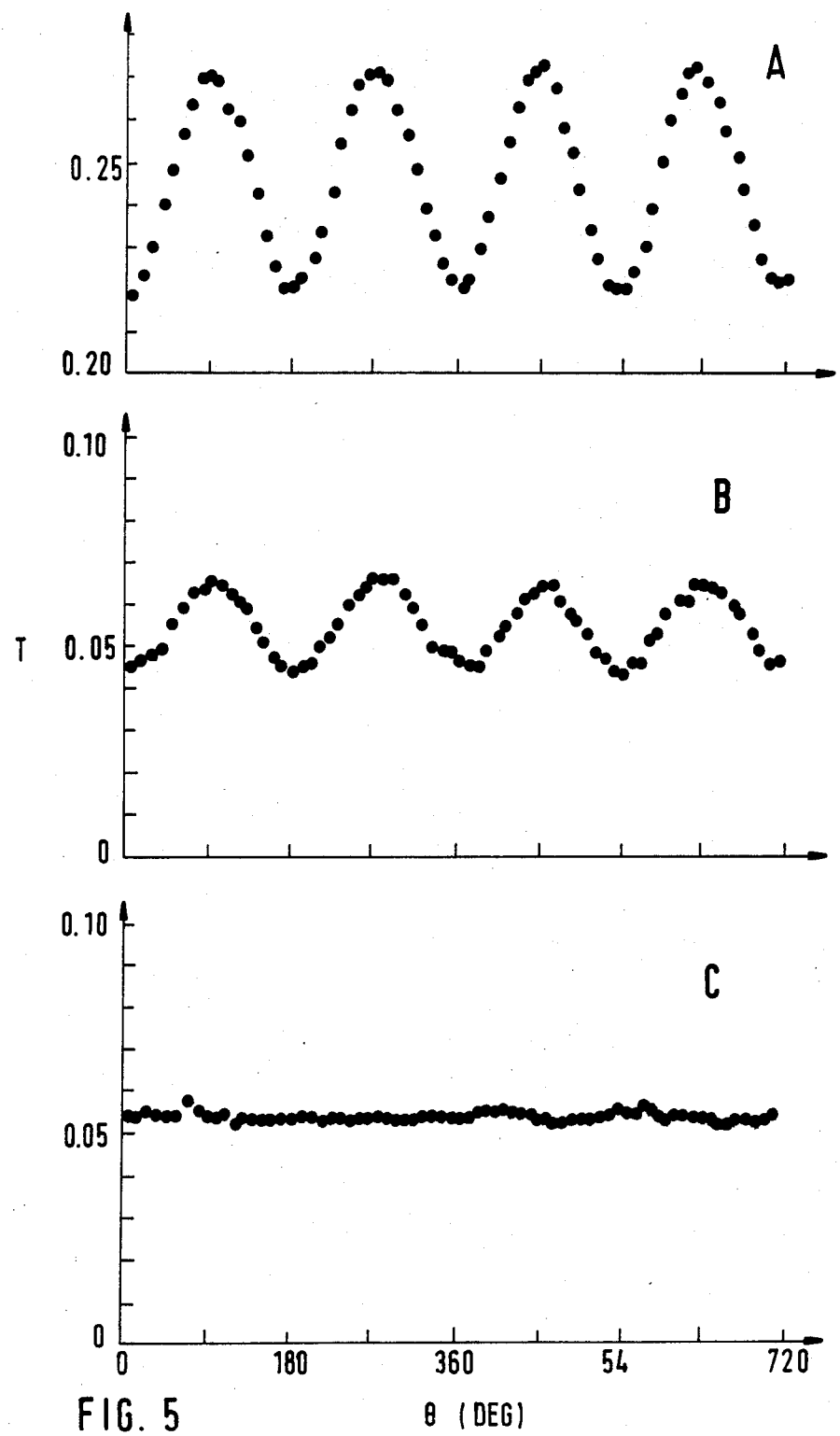
FIGS. 5(a) to 5(b) are graphs giving the transmission coefficient versus the angle $\theta$ between the incident wave plane of polarization and a paper sample having a known machine direction (M.D.), with a single sheet of paper (a); two sheets of paper with parallel M.D. (b) and two sheets of paper with perpendicular M.D. (c)

In the first experiment reported on FIG. 5(a), only one sample was mounted on the goniometer and the transmission-to-incident energy ratio T was determined while the sample angle was varied from 0° to 720° in 10° steps. The results reported in FIG. 5(a) shows a $\cos^2\theta$ behaviour where the amplitude, 11% of the average transmission, indicates that the paper is not ideal polarizer but a polarizer nonetheless.

In a second experiment, the samples had their machine direction parallel (see FIG. 5(b)) whereas, in a third experiment, the machine direction of the samples were crossed at 90° (see FIG. 5(c)). In the curves of FIG. 5(b) and 5(c), the average transmission is much lower because of the increased thickness. However, one can see from the relative amplitude of the variations (22% of the average transmission) that when the MD are parallel, the polarizing effect is enhanced while it diseappears when the MD are crossed.

(2) Other tests

In the other test results reported hereinafter, the incident and transmitted energies, were first determined without paper-sample, in both horizontal and vertical polarization, for normalization purposes.

Then, with vertical polarization and the paper in place, the beam pulses energy was measured while the transverse position of the sample was varied over a 30 cm span in 5 mm increments. Then the sample was moved back to its exact initial position and the measurements were repeated with horizontal polarization. The sample MD was usually horizontal. Repeated experiments have shown that the experimental device used by the inventors could measure 1% variations in energy and 0.2 mm displacements.

In such measurements, the spatial resolution on fibre orientation variations depends mostly on the SMM (submillimetre) laser beam size which can be varied from a few square millimetres to several square centimetres. Experimentation led the inventors to fix their choice on a geometry where 90% of the beam energy was concentrated within a 1 cm diameter circle, so that this geometry was kept for most of the work.

A first experiment was carried out on a sample made of narrow strips of paper mounted side by side. These strips were cut from paper sheets whose average fibre orientation had been previously measured with both the zero-span and the SMM laser technique. The results obtained by scanning this sample are shown on FIG. 6, together with the expected values from the previous measurements. These results confirm that the method according to the invention can detect abrupt variations of fibre orientations despite the rounding caused by beam size, provided that the variations are large enough. Average values on a small sample may vary significantly from values obtained over large areas.

Figure 7:
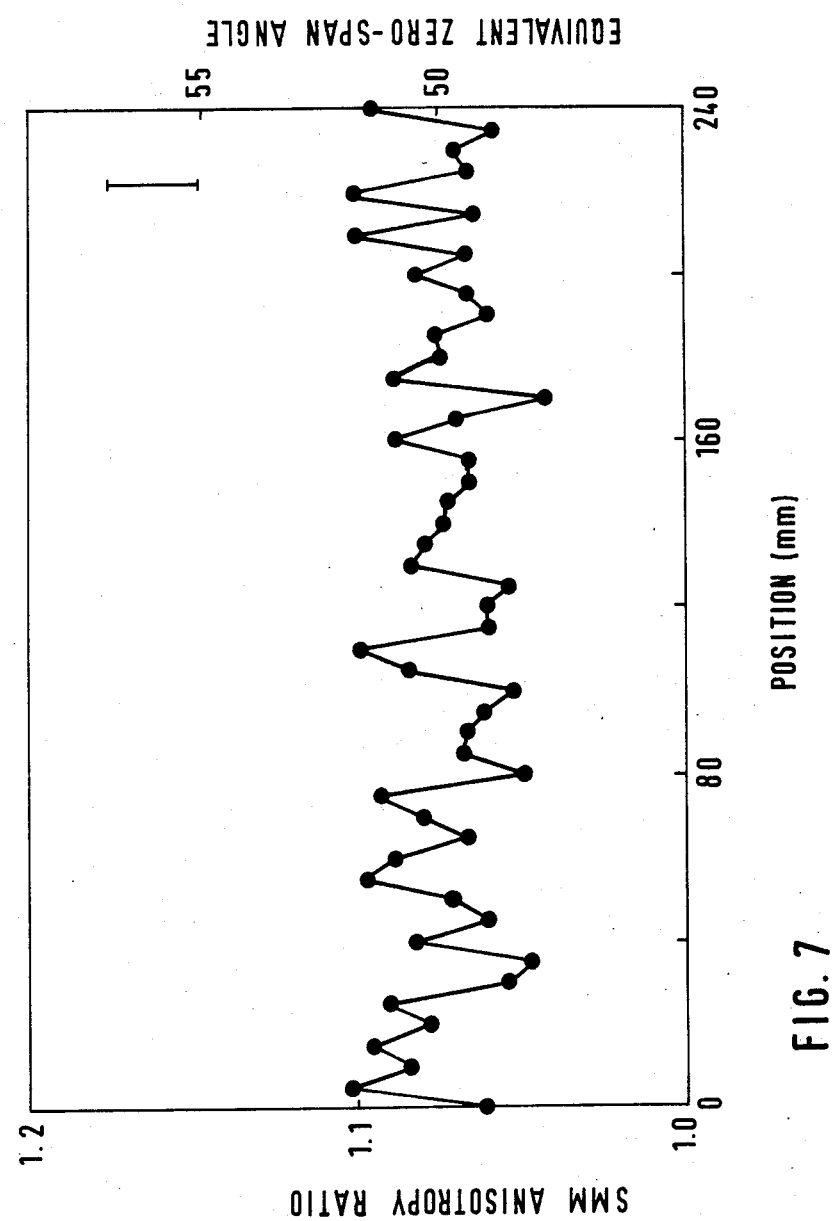
FIG. 7 is a graph showing the SMM anisotropy ratio as a function of position for a newsprint sample, the calculated equivalent zero-span angle being shown on the right axis.
Figure 8:
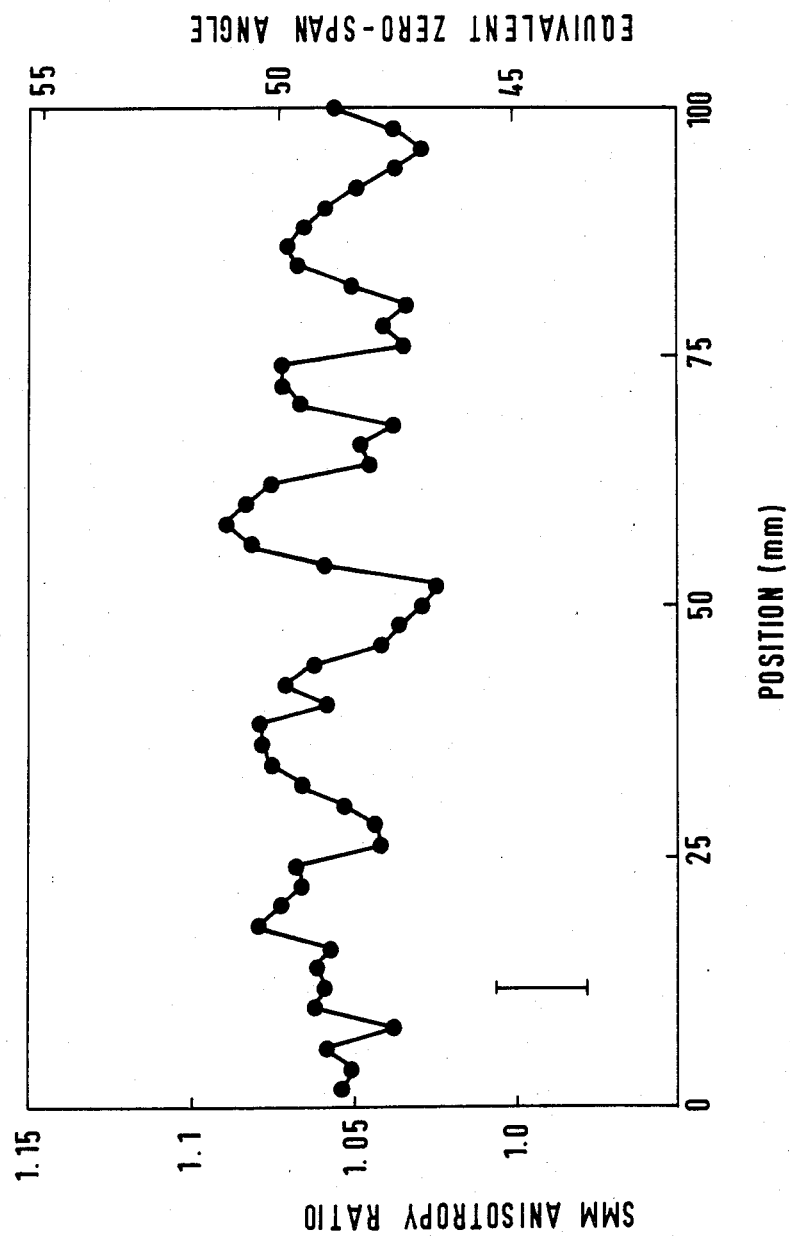
FIG. 8 is SMM anisotropy ratio as a function of position for a newsprint sample possibly affected by a periodic variation of fibre orientation.
Figure 9:
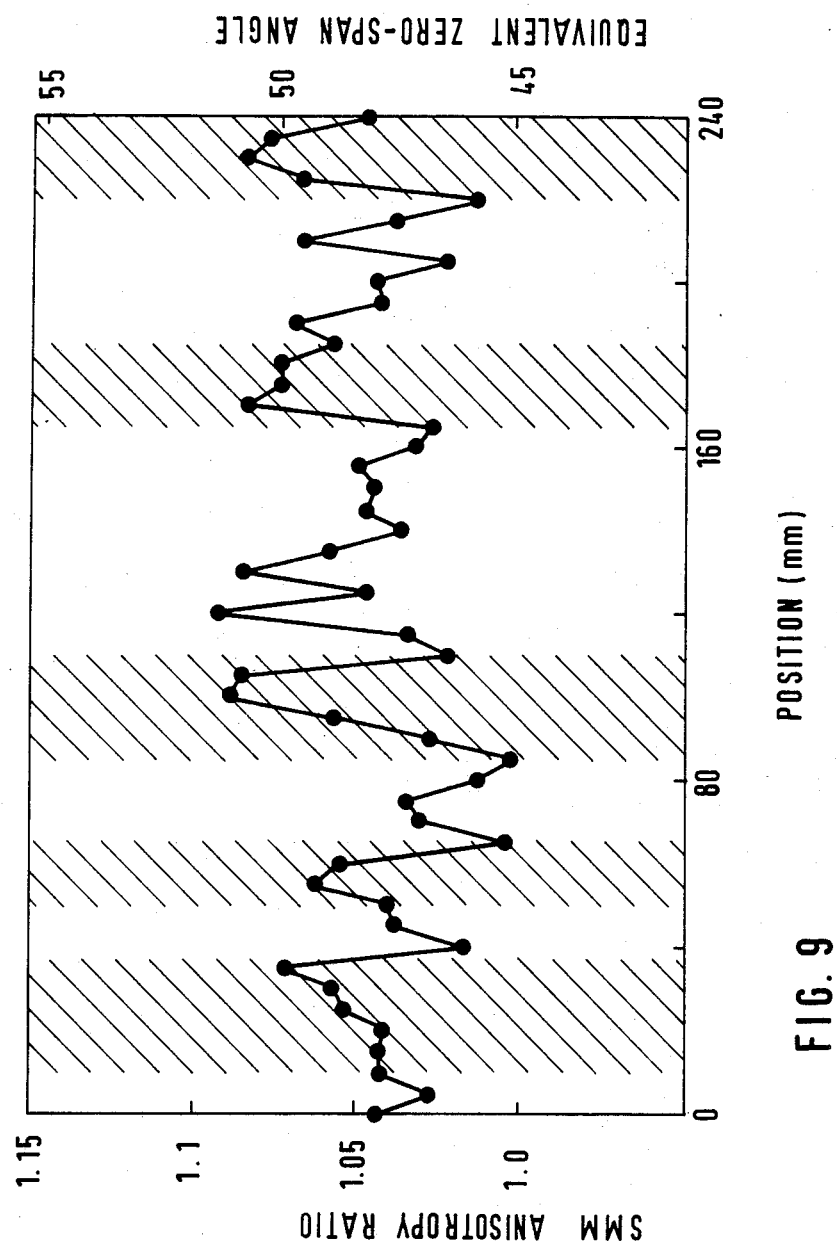
FIG. 9 is a graph showing the SMM anisotropy ratio as a function of position for a liner board sample showing visible surface streaks, the position of these streaks corresponding to the shaded areas.
Figure 10:
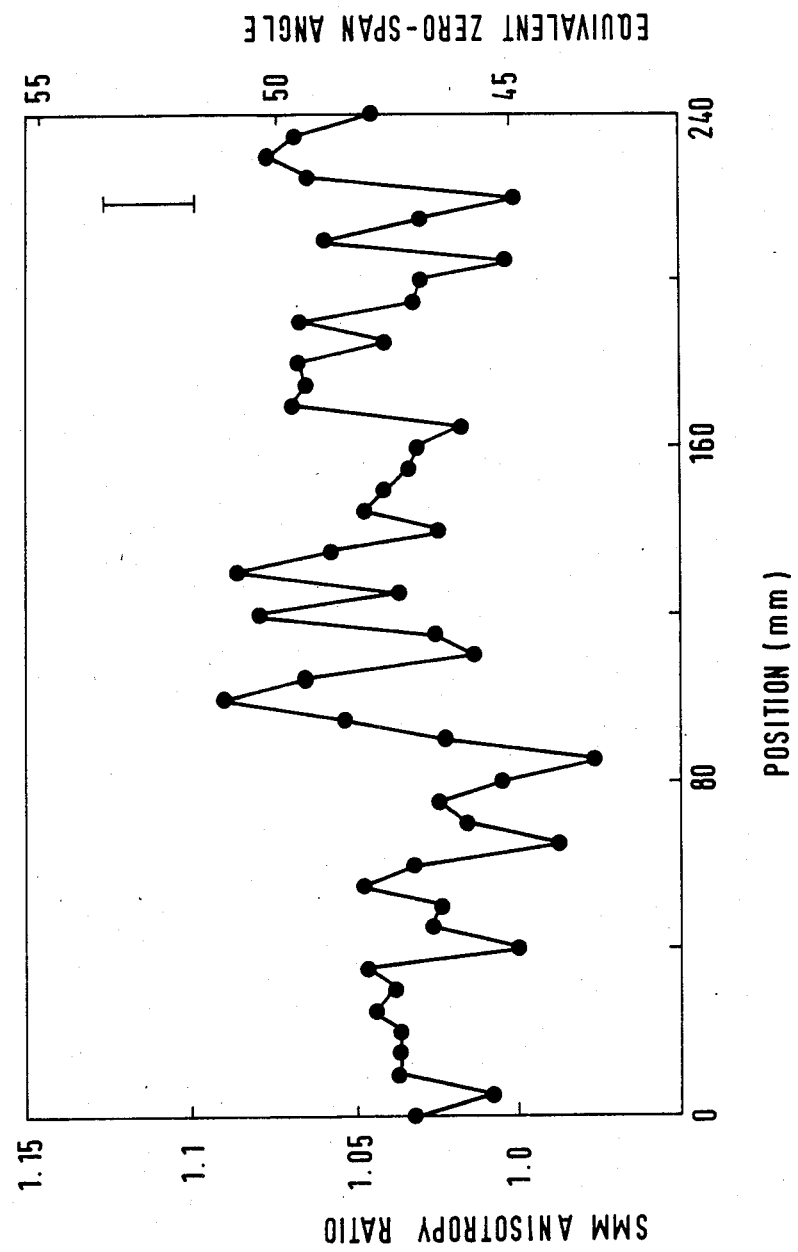
FIG. 10 is a graph showing the different measurement of the SMM ratio as a function of position for the same liner board sample.

Then, the same method using 70 microns waves, was applied to two different newspring samples (FIG. 7-8). On both graphs, the expected precision on the anisotropy ratio is shown. With a different wavelength, 119 microns, a liner board sample (165 g/m$^2$) was also tested (FIG. 9-10). On this last graph, the results of two different measurements made with the same sample at different times were plotted to illustrate the repeatability of the measuring technique.

Figure 6:
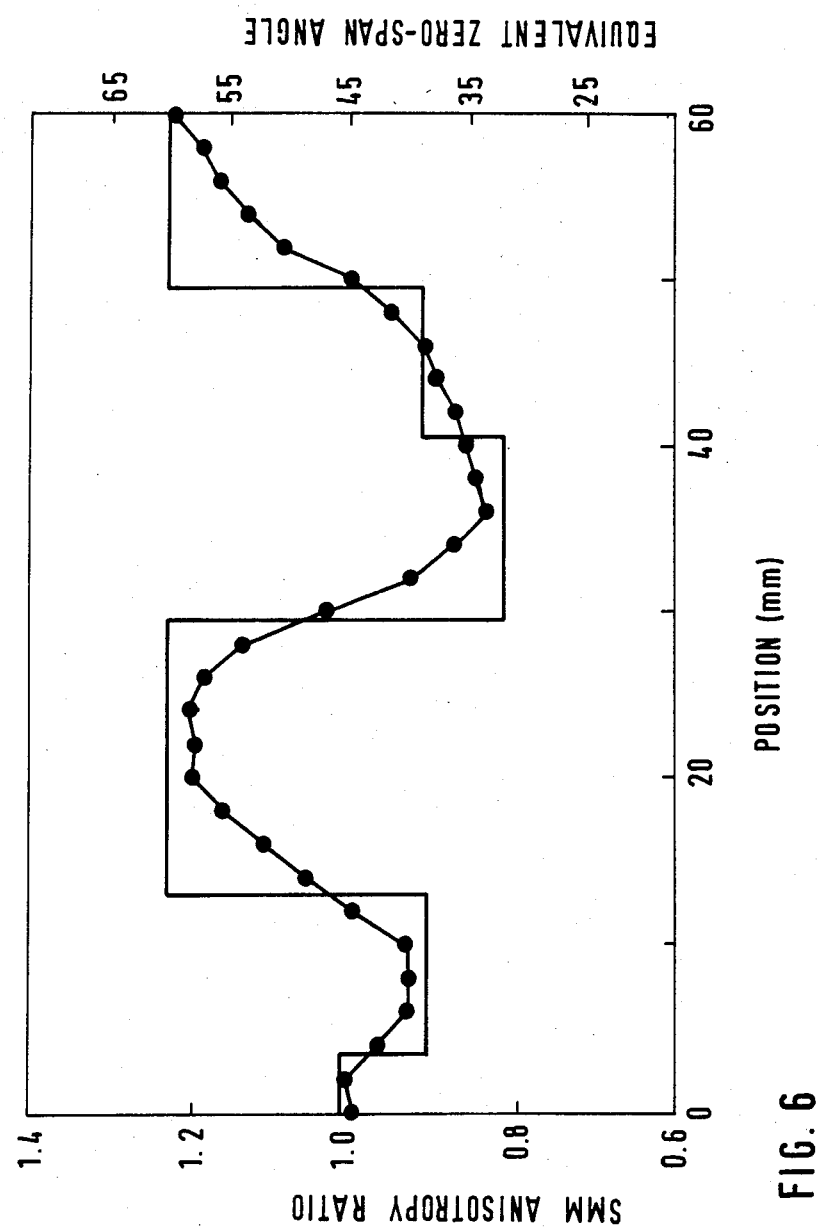
FIG. 6 is a graph showing the anisotropy ratio obtained by the submillimeter mesurement (SMM) according to the invention as a function of position for a sample made of six adjacent paper strips; the measured zero-span angle and strip widths for each paper strip being represented by the line segments.

The large variations of the SMM anisotropy coefficient as shown on FIG. 6 are caused by the fact that adjacent paper strips had their machine direction perpendicular to each other. The rounding effect of the beam size is clearly illustrated; it almost masks the presence of the 6 mm wide strip #5. This sets the lower limit of the spatial resolution achievable with such experimental conditions.

The results presented on FIG. 7 and FIG. 8 were both obtained with production newsprint scanned in machine direction. Fourier analysis of these anisotropy variations should reveal any periodic pattern. At first glance, the sample corresponding to FIG. 5 seems to be affected by a periodic variation of fibre orientation, the periodicity being close to 2.5 cm. This kind of information could lead to the actual cause of such a variation and its eventual elimination.

On the liner board sample whose fibre orientation variations are shown on FIG. 9, one could observe, under standard ligthing conditions, darker streaks crossing the SMM surveyed line. The position of those streaks correspond to the shaded areas on FIG. 8. There is some evidence of a relation between those streaks and fibre orientation variations, evidence that was confirmed in similar cases by microscopic photography. This experimental procedure yields fair repeatability as can be observed on FIG. 10 showing a different measurement made later on the same area of the same liner board sample.

As aforesaid, a major advantage of the method according to the invention is the fact that it is non-destructive, and inherently fast.

Another major advantage of the method according to the invention is its repeatability that was tested by performing the measurement on the same sample at a few weeks intervals. The comparison of these measurements has shown no significant difference between the various results.

A further major advantage of the method according to the invention is its precision which seems to be superior to that obtained with the well-known zero-span tensile strength test.

Another major advantage of the method according to the invention is that the beam traverses the fibrous structure whose anisotropy is to be measured even when this structure has a basis weight up to and even higher than 2000 g/m$^2$, thereby giving an indication of the average fibre orientation anisotropy through the whole thickness of the sample.

In the above description, reference has been made to energy detectors exclusively. It is however obvious for anyone skilled in the art that use could also be made of power detectors such as diodes, to determine the value of the ratio T.

What is claimed is:

1. A method for measuring the fibre orientation anisotropy in a fibrous structure, comprising the steps of:
    directing a linearly polarized, far-infrared laser beam towards one side of the fibrous structure whose fibre orientation anisotropy is to be measured;
    measuring the incident energy of said laser beam before it traverses the fibrous structure;
    measuring the transmitted energy of the laser beam on the other side of the fibrous structure with a first laser beam energy detector;
    determining the transmission coefficient T in at least two different orientations of the polarization plane of the laser beam with respect to the fibrous structure, said coefficient T being the ratio of the measured transmitted-to-incident energies;
    provided that both reflection and scattering of the laser beam by the fibrous structure remain small as compared to absorption and thereby that:

$$T=e^{-Ab}$$

where e is 2.71828; A is the absorption coefficient of the structure and b is the basis weight of said structure, calculating the ratio α of the absorption coefficients A measured in said at least two different orientations of the polarization plane of the laser beam; and
    using the so calculated absorption coefficient ratio α as a quantitative evaluation of the amount of anisotropy, the value of said absorption coefficient ratio α being equal to 1 when no anisotropy is present in the fibrous structure.

2. The method of claim 1, wherein use is made of a far-infrared laser beam having a wave length ranging from 50 to 2000 micrometers and wherein said method further comprises the steps of:
    diverting part of the incident energy of the laser beam towards a second laser beam energy detector;
    measuring said diverted incident energy with said second detector; and
    permanently using said diverted energy measured with said second detector to normalize the value of the incident energy measured before the laser beam traverses the fibrous structure.

3. The method of claim 2, comprising the additional step of:
    adjusting the laser beam size with a lens on the one side of said fibrous structure.

4. The method of claim 3, comprising the additional step of:
    rotating the fibrous structure with respect to the polarization plane of the laser beam in order to achieve said determination of the transmission coefficient T in at least two different orientations.

5. The method of claim 4 for use on a fibrous structure having a known machine direction and a known cross-direction, wherein the transmission coefficient T is determined in two orientations only of the polarization plane of the laser beam, one of said orientations being parallel to the machine direction of the structure, the other orientation being parallel to the cross-direction of said structure.

6. The method of claim 4, wherein the transmission coefficient T is determined in more than two orientations.

7. The method of claim 6, wherein the transmission coefficient T is determined in at least ten different orientations ranging from 0° to 90°.

8. The method of claim 3, comprising the additional step of:
    rotating the polarization plane of the laser beam with respect to the flat fibrous structure in order to achieve said determination of the transmission coefficient T in at least two different orientations.

9. The method of claim 8 for use on a fibrous structure having a known machine direction and a known cross-direction, wherein the transmission coefficient T is determined in two orientations only of the polarization plane of the laser beam, one of said orientations being parallel to the machine direction of the structure, the other orientation being parallel to the cross-direction of said structure.

10. The method of claim 8, wherein the transmission coefficient T is determined in more than two orientations.

11. The method of claim 10, wherein the transmission coefficient T is determined in at least ten different orientations ranging from 0° to 90°.

12. The method of claim 3, comprising the additional steps of:
    splitting the linearly polarized laser beam before it traverses the fibrous structure;
    modifying the angle of polarization of one splitted beam before it traverses the fibrous structure;
    measuring the transmitted energy of both splitted beams on the other side of the fibrous structure; and
    using the two measurements to determine two transmission coefficients T, each of said coefficient T corresponding to an orientation of the linearly polarized laser beam.

13. The method of claim 12 for use in a machine of manufacturing the fibrous structure, wherein one of said splitted beam is orientated in the machine direction of the fibrous structure and the other splitted beam in the cross-direction of said structure.

14. A device for measuring the fibre orientation anisotropy in a fibrous structure, said device comprising:
    a far-infrared laser for directing a laser beam towards one side of the fibrous structure whose fibre orientation anisotropy is to be measured;
    a linear polarizer for linearly polarizing the laser beam before it reaches the fibrous structure;

means for measuring the incident energy of the laser beam before it traverses the fibrous structure, a first laser beam energy detector for measuring the transmitted energy of said laser beam on the other side of the fibrous structure;

means for differently orientating the linearly polarized beam and fibrous structure with respect to each other; and processing means for determining the transmission coefficient T in at least two different orientations of the linearly polarized beam with respect to the fibrous structure, said coefficient T being the ratio of the transmitted-to-incident energies; and then, provided that both reflection and scattering of the laser beam by the fibrous structure remain small as compared to absorption and thereby that:

$$T = e^{-Ab}$$

where e is 2.71828; A is the absorption coefficient of the structure and b is the basis weight of said structure, calculating the ratio $\alpha$ of the absorption coefficients A in said at least two different orientations of the linearly polarized beam, said ratio $\alpha$ giving a quantitative evaluation of the amount of anisotropy present in the fibrous structure.

15. The device of claim 14 wherein the far-infrared laser is a laser emitting a beam with a wave length ranging from 50 to 2000 micrometers wherein said device further comprises:

a beam splitter to divert part of the incident energy towards a second laser beam energy detector; and means for normalizing the value of the incident energy measured with said measuring means, with the value of said diverted energy measured with said second detector prior to supplying said value of the incident energy in said processing means.

16. The device of claim 15, wherein said means for measuring the incident energy consists of said first laser beam energy detector.

17. The device of claim 15, further comprising:

a lens for adjusting the laser beam size on the one side of the fibrous structure.

18. The device of claim 17, further comprising:

means for rotating the flat fibrous structure with respect to the linearly polarized laser beam in order to achieve said determination of coefficient T in at least two different orientations.

19. The device of claim 18, wherein said rotating means is a goniometer.

20. The device of claim 17 for use in measuring the fibre orientation anisotropy in a fibrous structure having a known machine direction and a known cross-direction, further comprising:

another beam-splitter to split the linearly polarized beam before it traverses the fibrous structure;

means for rotating at 90° the angle of polarization of one splitted beam before it traverses the fibrous structure;

two separate detectors both acting as said first laser beam energy detector, for measuring the transmitted energy of both beams, respectively, on the other side of the fibrous structure; and means to supply the value of the transmitted energy of each of said beams to the processing means so that two transmission coefficients T be calculated, one of said coefficient T corresponding to the machine direction of the fibrous structure, the other coefficient T to the cross-direction of said structure.

21. The device of claim 17, further comprising:

means for rotating the polarization plane of the laser beam in order to achieve said determination of coefficient T in at least two different orientations.

22. The device of claim 17, for use in measuring the fibre orientation anisotropy in a fibrous structure having a known machine direction and a known cross-direction, further comprising:

another far-infrared laser for directing a laser beam parallel to the laser beam of the one laser toward the one side of the fibrous structure;

another linear polarizer for linearly polarizing the laser beam of said another laser before its reaches the structure in a direction perpendicular to the polarization plane of the one laser beam;

two separate detectors both acting as said first laser beam energy detector, for measuring the transmitted energy of both of said beams, respectively, on the other side of the fibrous structure; and means to supply the value of the transmitted energy of each of said beams to the processing means so that two transmission coefficients T be calculated, one of said coefficient T corresponding to the machine direction of the fibrous structure, the other coefficient T to the cross-direction of said structure.

* * * * *

UNITED STATES PATENT AND TRADEMARK OFFICE
CERTIFICATE OF CORRECTION

PATENT NO. : 4,654,529
DATED : March 31st, 1987
INVENTOR(S) : Russell BOULAY et al Page 1 of 2

It is certified that error appears in the above-identified patent and that said Letters Patent is hereby corrected as shown below:

IN THE SPECIFICATION:

Column 1, line 61: "hold" should read --held--;

Column 2, line 39: "in line" should read --on line--;
          line 42: "young's" should read --Young's--;

Column 3, line 44: the period after the word "anisotropy" should be replaced by a comma;

Column 5, line 18: "5(b)" should read --5(c)--;
          line 42: "the" should read --a--;

Column 6, line 3: "made" should read --mode--;
          line 8: "wave length" should read --wavelength--;
          line 13: "in" should read --that--;

Column 8, line 13: "whis" should read --this--;
          line 15: "rorated" should read --rotated--;
          line 23: "15" should read --25--;

Column 10, line 2: the comma should be deleted;
           line 32: "this last graph" should read --these last graphs--;
           line 48: "Fig. 5" should read --Fig. 8--;
           line 58: "Fig. 8" should read --Fig. 9--;

UNITED STATES PATENT AND TRADEMARK OFFICE
CERTIFICATE OF CORRECTION

PATENT NO. : 4,654,529

DATED : March 31st, 1987

INVENTOR(S) : Russell BOULAY et al

Page 2 of 2

It is certified that error appears in the above-identified patent and that said Letters Patent is hereby corrected as shown below:

IN THE CLAIMS:

Claim 2, line 2: "wave length" should read --wavelength--;

Claim 13, line 1: replace "of" second occurence, by --for--.

Signed and Sealed this

Eighteenth Day of August, 1987

Attest:

DONALD J. QUIGG

Attesting Officer

Commissioner of Patents and Trademarks